US006020380A

United States Patent [19]
Killian

[11] Patent Number: 6,020,380
[45] Date of Patent: Feb. 1, 2000

[54] METHOD OF TREATING CHRONIC OBSTRUCTIVE PULMONARY DISEASE

[75] Inventor: Anthony Killian, Pittsburgh, Pa.

[73] Assignee: Tap Holdings Inc., Deerfield, Ill.

[21] Appl. No.: 09/200,037

[22] Filed: Nov. 25, 1998

[51] Int. Cl.$^7$ .................................................. A61K 31/19
[52] U.S. Cl. ............................................................ 514/570
[58] Field of Search ............................................. 514/570

[56] References Cited

U.S. PATENT DOCUMENTS

| | | | |
|---|---|---|---|
| 4,808,627 | 2/1989 | Ogletree | 514/469 |
| 4,851,586 | 7/1989 | Bundy et al. | 568/633 |
| 4,939,169 | 7/1990 | Bundy et al. | 514/459 |
| 5,021,448 | 6/1991 | Piraino et al. | 514/415 |
| 5,096,916 | 3/1992 | Skupin | 514/401 |
| 5,180,742 | 1/1993 | Terao et al. | 514/558 |
| 5,304,658 | 4/1994 | Terao et al. | 549/80 |
| 5,534,548 | 7/1996 | Killian | 514/545 |

OTHER PUBLICATIONS

*American Thoracic Society*, "Standards For the Diagnosis and Care of Patients With Chronic Obstructive Pulmonary Disease (COPD) and Asthma", pp. 225–343, (Nov. 1986).

A. Bruist, et al., *Chest*, "Chronic Obstructive Pulmonary Disease Early Intervention Trial (Lung Health Study)" 103(6): pp. 1863–1872, (Jun. 1993).

J. E. Connett, et al., *Controlled Clinical Trials*, "Design of the Lung Health Study: A Randomized Clinical Trial of Earl Intervention for Chronic Obstructive Pulmonary Disease", 14: pp. 3S–19S, (1993).

*American Journal of Respiratory and Critical care Medicine*, "Definitions, Epidemiology, Pahtophysiology, Diagnosis, and Staging", vol. 152: pp. 578–583, (1995).

*Primary Examiner*—James H. Reamer
*Attorney, Agent, or Firm*—Jerry F. Janssen

[57] ABSTRACT

A class of Ω-substituted-1,4-benzoquinon-2-yl]alkanoic acids are useful in the treatment of chronic obstructive pulmonary disease (COPD). The preferred compound for the method of treatment is 7-(3,5,6-trimethyl-1,4-benzoquinon-2-yl)-7-phenylheptanoic acid or a pharmaceutically acceptable salt, ester or pro-drug thereof.

24 Claims, 21 Drawing Sheets

METHOD OF TREATING CHRONIC OBSTRUCTIVE PULMONARY DISEASE

TECHNICAL FIELD

The present invention relates to a method of medical treatment. More particularly, the present invention concerns the use of certain Ω-substituted (1,4-benzoquinon-2-yl)-alkanoic acids for the treatment of chronic obstructive pulmonary disease.

BACKGROUND OF THE INVENTION

Although the prevalence of chronic obstructive pulmonary disease (COPD) is not known, it is estimated that approximately 14 million persons in the United States suffer from the condition, with the estimated number having increased some 42% between 1982 and 1995. Estimates of COPD in population-based studies in the United States range between 4% to 6% of adult white males and from 1% to 3% of adult white females.

In 1991, there were 85,444 deaths due to COPD and allied conditions, a death rate of 18.6 per 100,000 persons, ranking the condition as the fourth leading cause of death in the United States.

In the past, therapeutic methods for the treatment of COPD included the administration, typically by means of a metered dose inhaler (MDI), of a sympathomimetic bronchodilator such as ephedrine, epinephrine, or isoproterenol. The use of these agents, however, has been replaced more recently by more $\beta_2$-specific bronchodilators such as metaproterenol, albuterol, terbutaline, and bitolterol, generally administered as aerosols.

Oral sustained-release formulations of theophylline are generally given for chronic maintenance therapy. Although the benefits of theophylline treatment in patients with COPD are generally difficult to prove, this form of treatment remains popular.

Anticholinergics such as atropine sulfate and ipratroprium, a quaternary ammonium derivative of atropine, have been used for the inhalation treatment of COPD, although the former is not approved for use. Because of its quaternary ammonium salt nature, ipratroprium is minimally absorbed into the blood stream and has fewer side effects than atropine.

Inhaled corticosteroids are often effective for mild to moderate asthmatics, whereas such use has been shown to be efficacious in only a small percentage of COPD patients.

Because of the wide prevalence of chronic obstructive pulmonary disease, and its high ranking among the leading causes of death, there is a continuing need for the discovery and development of new agents for the treatment and amelioration of the disease.

U.S. Pat. No. 5,180,742 and its division, U.S. Pat. No. 5,304,658, both to Terao, et al., disclose a class of quinone derivatives for use in the inhibition of lipid peroxidase activity, as antagonists of thromboxane $A_2$ receptors, or as inhibitors of the activity of 5-lipoxygenase activity.

U.S. Pat. No. 5,534,548 to Killian discloses the use of a class of substituted (Ω-1,4-benzoquinon-2-yl)-alkanoic acids for the treatment or prevention of eclampsia or preeclampsia in pregnant women.

SUMMARY OF THE INVENTION

In accordance with the present invention, there is provided a method of treating chronic obstructive pulmonary disease comprising the administration to a patient in need of such treatment a therapeutically effective amount of a compound, or pharmaceutically acceptable salt thereof, having the structure:

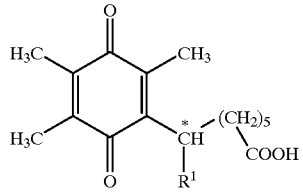

wherein the asterisk denotes a chiral center, and $R^1$ is selected from the group consisting of unsubstituted phenyl; and phenyl substituted with one or more groups independently selected from halo, hydroxy, alkyl of one to three carbon atoms, and alkoxy of one to three carbon atoms.

BRIEF DESCRIPTION OF THE DRAWING FIGURES

DETAILED DESCRIPTION OF THE PREFERRED EMBODIMENTS

Definitions

As used throughout this specification and the appended claims, the following terms have the meanings ascribed.

The term "treatment" means the alleviation of the symptoms of chronic obstructive pulmonary disease and/or preservation of lung function and/or the general improvement in the patient's perceived quality of life as regards the disease conditions and symptoms.

The distinctions among the definitions of airway obstruction, chronic bronchitis, chronic obstructive bronchitis, pulmonary emphysema, chronic obstructive emphysema, chronic asthmatic bronchitis, and chronic obstructive pulmonary disease are elegantly presented in "The Merck Manual," 16$^{th}$ Ed., pp. 658–659, Merck Research Laboratories, Rahway, N.J., 1992, and is hereby incorporated by reference.

The term "airway obstruction" refers to an increased resistance to airflow exhibited by characteristic spirometric findings.

The term "chronic bronchitis" refers to the condition associated with prolonged exposure to nonspecific bronchial irritants and is accompanied by mucus hypersecretion and structural changes in the bronchi.

The term "chronic obstructive bronchitis" means the disease condition frequently associated with the symptoms of chronic bronchitis in which disease of the small airways has progressed to the point that there is clinically significant airway obstruction.

The term "pulmonary emphysema" refers to enlargement of the airspaces distal to the terminal nonrespiratory bronchioles, accompanied by destructive changes of the alveolar walls.

The term "chronic obstructive emphysema" refers to the condition when there has been sufficient loss of lung recoil to allow marked airway collapse upon expiration, leading to the physiologic pattern of airway obstruction.

The term "chronic asthmatic bronchitis" refers to an underlying asthmatic condition in patients in whom asthma has become so persistent that clinically significant chronic airflow obstruction is present despite antiasthmatic therapy.

The term "chronic obstructive pulmonary disease", or "COPD", is defined as a generally progressive disease state, due to chronic obstructive bronchitis or chronic obstructive emphysema, which may be accompanied by airway hyperreactivity and may be partially reversible.

The complex relationships among the definitions of chronic bronchitis, emphysema, asthma, and COPD can be more readily seen by referring to the diagrammatic scheme of diseases of the air passage adapted from *Am. J. Respiratory and Critical Care Med.*, 152: S78–S83 (1995) and shown in FIG. 1.

Figure 1:
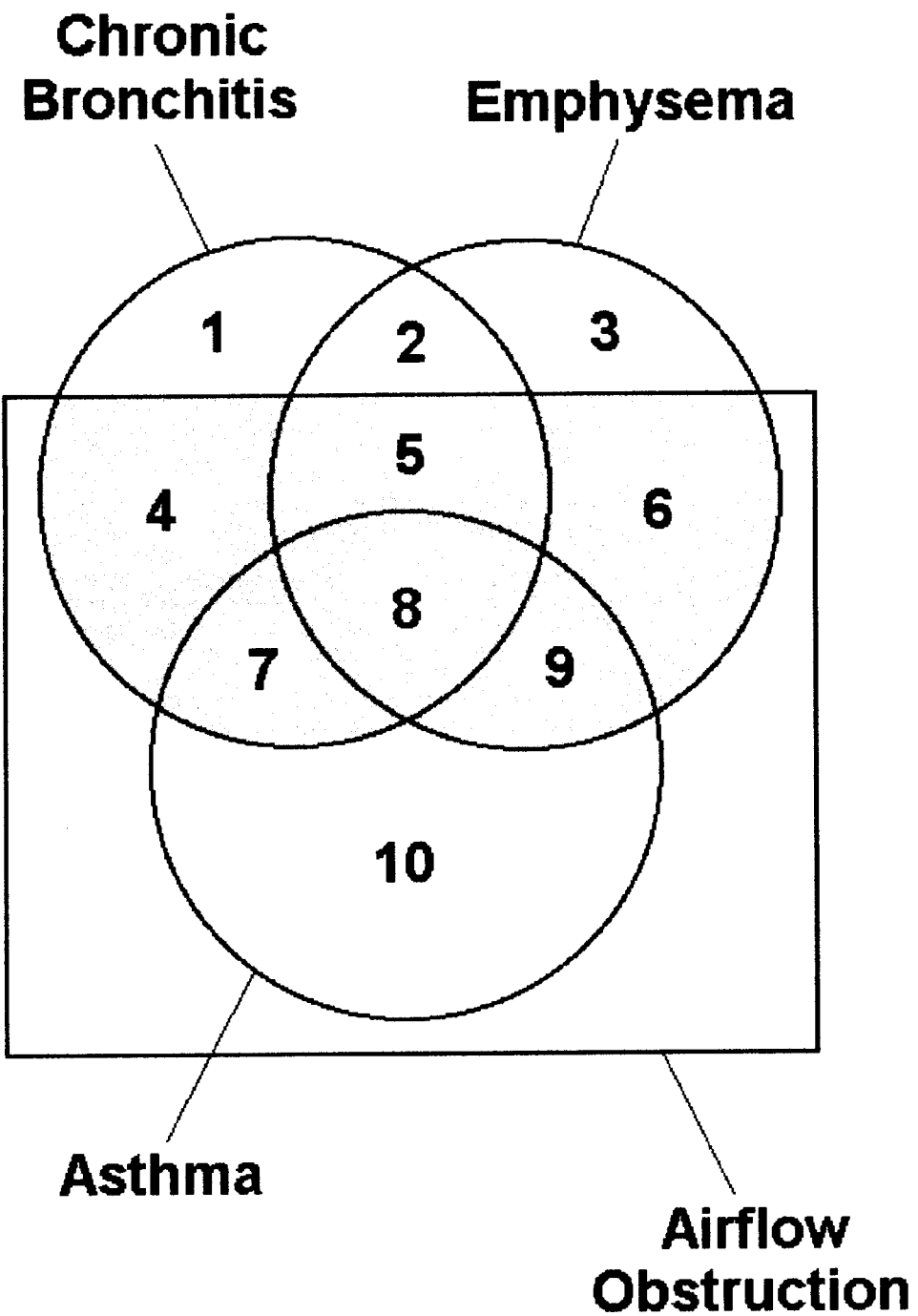
FIG. 1 is a Venn diagram of various pulmonary disease conditions illustrating the scope of the definition of chronic obstructive pulmonary disease for the purpose of the present invention.

In FIG. 1, a Venn diagram shows various sets of patient populations, with the graphical representations of the subsets in the diagram not intended to represent actual patient populations. In the diagram, patient populations with chronic bronchitis, emphysema, and asthma are represented as falling within one of the three indicated overlapping circles. Patients suffering airflow obstruction fall within the rectangular box. Patients having chronic obstructive pulmonary disease (COPD) are those falling within the shaded subset classifications.

Patients not experiencing airflow obstruction, but having chronic bronchitis (subset 1), emphysema (subset 3) or both (subset 2), are not included in the definition of COPD. Likewise, those with asthma whose airflow obstruction is completely reversible (subset 10) are not considered to have COPD.

In many cases, however, it is not possible to easily differentiate asthmatic patients with airflow obstruction which does not remit completely, from patients with chronic bronchitis and emphysema who have partially reversible airflow obstruction with airway hyperreactivity. Thus, patients with unremitting asthma (subsets 7, 8, and 9) are classified as having COPD.

Chronic bronchitis and emphysema with airflow obstruction often occur together (subset 5) and some patients may also have asthma associated with these two disorders (subset 8).

The acronyms for spirometric measurements are those generally used in the medical community. "FEV$_1$" means the forced expiratory volume over one second as measured by standard spirometric techniques.

"FVC" means the forced vital capacity and "MVV$_{12}$" means maximal voluntary ventilation in twelve seconds, both as also measured by spirometry.

Compounds of the Method of the Present Invention

The compounds contemplated as falling within the scope of the method of the present invention are selected from those defined by the generic formula I given above in the Summary of the Invention, or a pharmaceutically acceptable salt or prod-rug thereof. The preferred compound of the method of the present invention is (±)-7-(3,5,6-trimethyl-1, 4-benzoquinon-2-yl)-7-phenylheptanoic acid (known generically as seratrodast), or a pharmaceutically acceptable salt thereof or pro-drug and includes individual enantiomers and mixtures thereof, including the racemic mixture. Both compounds were shown to be systemically available following oral administration, and pre-clinical pharmacology studies show that both enantiomers are pharmacologically active.

Compounds of the present invention are prepared by the methods detailed in U.S. Pat. Nos. 5,180,742, and 5,304, 658, the contents of which are incorporated herein by reference. The isolation of either the R(+)- or S(−)-enantiomeric forms of the compounds is carried out by techniques well known in the art such as conventional formation of a mixture of diastereomeric salts with an optically active base such as (−)-1-phenylethylamine, (+)-1-phenylethylamine, or the like, followed by selective recrystallizations and regeneration of the free acid form of the compounds from their separated diastereomeric salts. Alternatively, the compounds can be separated on chiral chromatographic columns or by reverse phase HPLC using methods also well known in the art.

The carboxylic acid function of compounds of the present invention is converted to a pharmaceutically acceptable salt by dissolution in an appropriate solvent and subsequent neutralization with the selected base. As used herein, the term "pharmaceutically acceptable salt" refers to those salts which are within the scope of sound medical judgment, suitable for use in contact with the tissues of humans without undue toxicity, irritation, allergic response and the like, and are commensurate with a reasonable benefit/risk ratio.

Pharmaceutically acceptable salts are well known in the pharmaceutical formulation art. For example, S. M. Berge, et al. describe pharmaceutically acceptable salts in detail in *J. Pharmaceutical Sciences,* 66: 1–19 (1977), the contents of which are incorporated herein by reference. The salts can be prepared in situ during the final isolation and purification of the compounds of the invention, or separately by reacting the free acid function with a suitable inorganic or organic base.

Representative pharmaceutically acceptable salts of the compounds utilized in the method of this invention include alkali or alkaline earth metal salts such as aluminum, calcium, sodium, lithium, potassium, magnesium and zinc salts and the like. Further pharmaceutically acceptable salts include, when appropriate, nontoxic ammonium, quaternary ammonium, and amine cations formed with the carboxyl function of the compounds contemplated for use in the method of the invention.

The compounds contemplated for use in the method of the present invention may also be administered in the form of a pharmaceutically acceptable pro-drug. The term "pro-drug" refers to compounds that are rapidly transformed in vivo to yield the parent compounds of Formula (I), as for example, by hydrolysis in blood. T. Higuchi and V. Stella provide a thorough discussion of the pro-drug concept in "Pro-drugs as Novel Delivery Systems," Vol. 14 of the A.C.S. Symposium Series, American Chemical Society (1975).

Examples of esters, for example, useful as pro-drugs for compounds containing carboxyl groups may be found on pages 14–21 of *Bioreversible Carriers in Drug Design: Theory and Application,* edited by E. B. Roche, Pergamon Press (1987).

The term "pro-drug ester group" refers to any of several ester-forming groups that are hydrolyzed under physiological conditions. Examples of pro-drug ester groups include pivaloyloxymethyl, acetoxymethyl, phthalidyl, indanyl and methoxymethyl, as well as other such groups known in the art.

Pharmaceutical Compositions

Pharmaceutical compositions for use in the method of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; oils such as peanut oil, cottonseed oil, safflower oil, sesame oil, olive oil, corn oil and soybean oil, glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of the formulator. The pharmaceutical compositions of this invention can be administered to humans orally, parenterally, subcutaneously, or as an inhalation spray.

Liquid dosage forms for oral administration include pharmaceutically acceptable emulsions, microemulsions, solutions, suspensions, syrups and elixirs. In addition to the active compound, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug administered intramuscularly or subcutaneously, it is often desirable to slow the absorption of the drug following injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, 9 g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Powders and sprays can contain, in addition to the active compound of this invention, excipients such as lactose, talc, silicic acid, aluminum hydroxide, calcium silicates and polyamide powder, or mixtures of these substances. Sprays can additionally contain customary propellants such as chlorofluoro-hydrocarbons.

Therapeutic Administration

According to the method of treatment of the present invention, conditions subsumed under the above definition of chronic obstructive pulmonary disease (COPD) are treated in a patient in need of such treatment by administering to the patient a therapeutically effective amount of a compound of the invention, in such amounts and for such time as is necessary to achieve the desired result. By a "therapeutically effective amount" of a compound of the invention is meant a sufficient amount of the compound to effectively ameliorate the course of the disease and/or alleviate one or more symptoms of COPD, or improve the quality of life in a patient at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the severity of the disorder; the activity of the compound employed; the specific composition employed; the age, body weight, general health, sex and diet of the patient; the time of administration, route of administration, and rate of excretion of the compound employed; the duration of the treatment; drugs used in combination or coincidental with the specific compound employed; and like factors well known in the medical arts. Since some of these parameters vary from patient to patient, it is a well-known technique utilized by medical practitioners to determine the proper dose for a particular patient by "dose titrating" the patient; that is, by using the technique of starting with a dose lower than that required to obtain the desired effect, and gradually increasing the dose over time until the desired therapeutic benefit is obtained.

The total daily dose of the compounds of this invention administered to a human or other mammal in single or in divided doses can be in amounts ranging between about 0.5 mg/kg to about 20 mg/kg of body weight. Single dose compositions may contain such amounts or sub-multiples thereof to make up the daily dose. In general, treatment regimens according to the present invention comprise administration to a patient in need of such treatment from about 50 mg to about 1000 mg, or more typically from about 250 mg to about 800 mg of the compound(s) of this invention per day in single or multiple doses.

Therapeutic Activity

In a randomized, double-blind, parallel-group study conducted with 498 patients suffering moderate to severe COPD, a representative compound of the present invention, ($\pm$)-7-(3,5,6-trimethyl-1,4-benzoquinon-2-yl)-7-phenylheptanoic acid, (seratrodast) demonstrated improvement over baseline values in the patient group receiving seratrodast in improvement in $FEV_1$ scores and patient perceived measures of such symptoms as cough, chest tightness, shortness of breath, and wheezing as demonstrated by the data graphically represented in FIGS. 2 to 21.

The study consisted of a two-week placebo lead-in period, followed by a fourteen-week double-blind treatment period. At the end of the two-week placebo lead-in period, eligibility of patients for entry into the fourteen-week double-blind period of the study was determined based upon study screening admission criteria and a review of the patient's diary entries and dosing compliance during the two-week lead-in.

During the fourteen-week double-blind period of the study, pre- and post-exercise dyspnea scores, spirometric measurements (including $FEV_1$, FVC, and $MVV_{12}$), COPD Overall Symptom Scale, cough and sputum index, and exercise capacity were measured prior to dosing on each visit.

In the treatment period, patients were randomized into groups receiving placebo, 80 mg, 160 mg, and 240 mg of seratrodast. Table 1 shows the distribution of patients among the groups receiving placebo and various doses of the test compound.

TABLE 1

Patient Population Groups in the Study

| Study Group | No. of Patients | Medication Received |
| --- | --- | --- |
| 1 | 119 | 240 mg/day Seratrodast |
| 2 | 127 | 160 mg/day Seratrodast |
| 3 | 125 | 80 mg/day Seratrodast |
| 4 | 127 | Placebo |

The patients were allowed to use theophylline and ipratroprium if they had been receiving those medications at the time of initiation of the study. All patients were provided with inhaled β-agonist, albuterol (Ventolin) with instructions to use this medication on an as-needed basis. However, patients were instructed to refrain from using the albuterol eight hours prior to each study visit. In the event the patient did not comply with these dosing instructions, the study visit for that patient was rescheduled.

Primary study end points included six minute walk and combined symptom scores (wheezing, dyspnea, chest tightness, cough). Secondary endpoints included measures of lung function ($FEV_1$, FVC, $MVV_{12}$) Guyatt's quality of life questionnaire, and cough and sputum index questionnaire. Patients were also asked to report daily and nocturnal symptoms, β-agonist usage, and AM and PM peak expiratory flow rate (PEFR) in a diary.

COPD Study Results

Exercise capacity (distance covered in a 6-minute walk), dyspnea scores, pulmonary function (spirometric) testing, including $FEV_1$, FVC, and $MVV_{12}$, were performed at the start and end of the single-blind lead-in period, and at two- to four-week intervals throughout the study.

Figure 2:
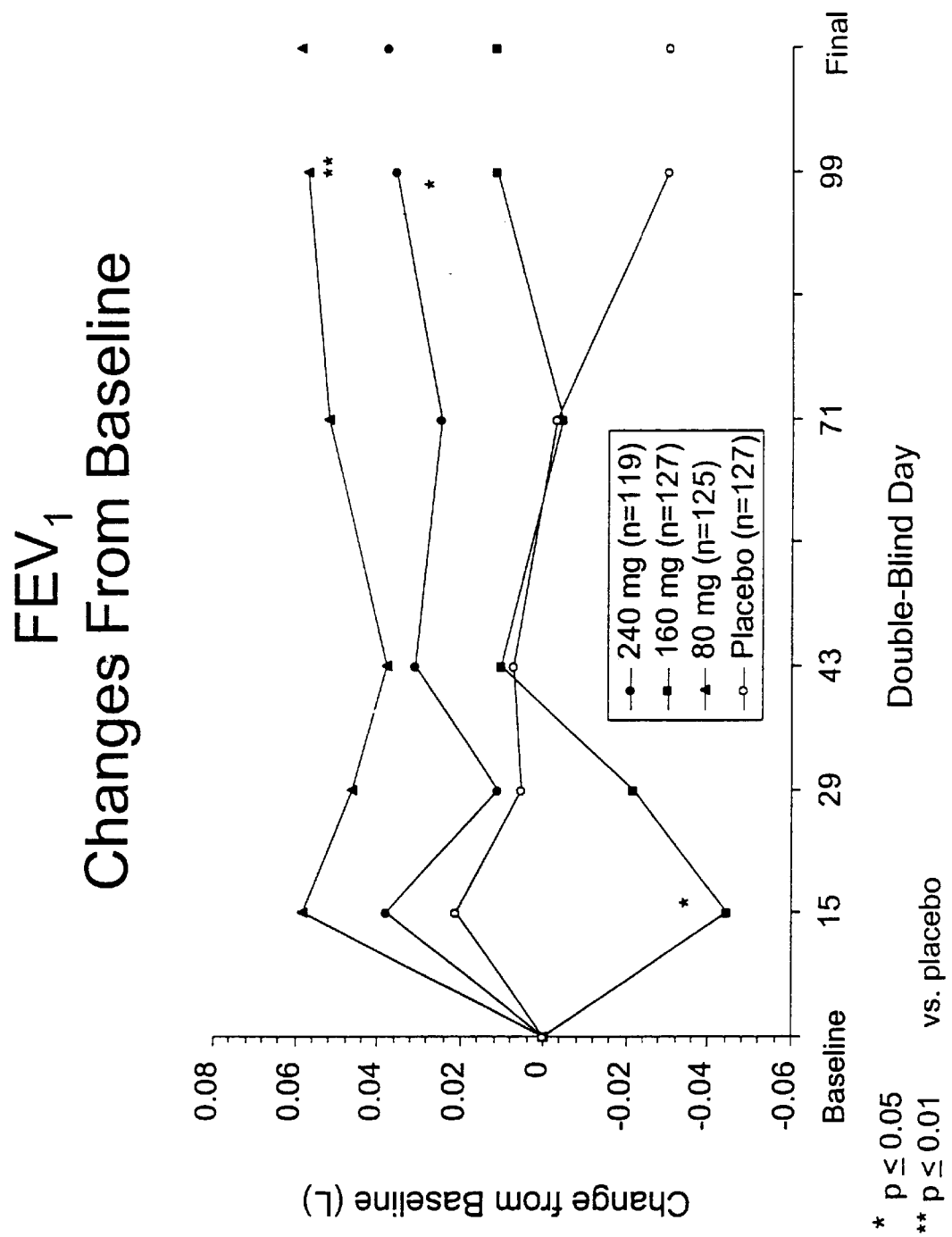
FIG. 2 is a graphical representation of forced expiratory volume in one second ($FEV_1$) of patients taking part in the study.

Normal subjects have an $FEV_1$ between 2.5–3.0 liters/sec depending upon their size, gender and age. The patients enrolled in this trial had an average baseline $FEV_1$ of 1.15 liters/sec. Over the first four weeks of the study, patients receiving seratrodast demonstrated a clinically significant improvement in lung function as measured by $FEV_1$. This improvement in lung function was preserved for the entire duration of the study, such that there was a difference (based upon mean values) of approximately 42–88 mL in $FEV_1$ between the placebo and the treated groups (FIG. 2). In COPD, patients receiving standard care show a progressive deterioration of lung function, measured as $FEV_1$, of between 60 and 120 mL per year. The improvement obtained by administration of seratrodast according to the invention produced a dramatic and meaningful improvement in lung function which, if maintained, will improve the patient's overall health status and mortality.

Figure 3:
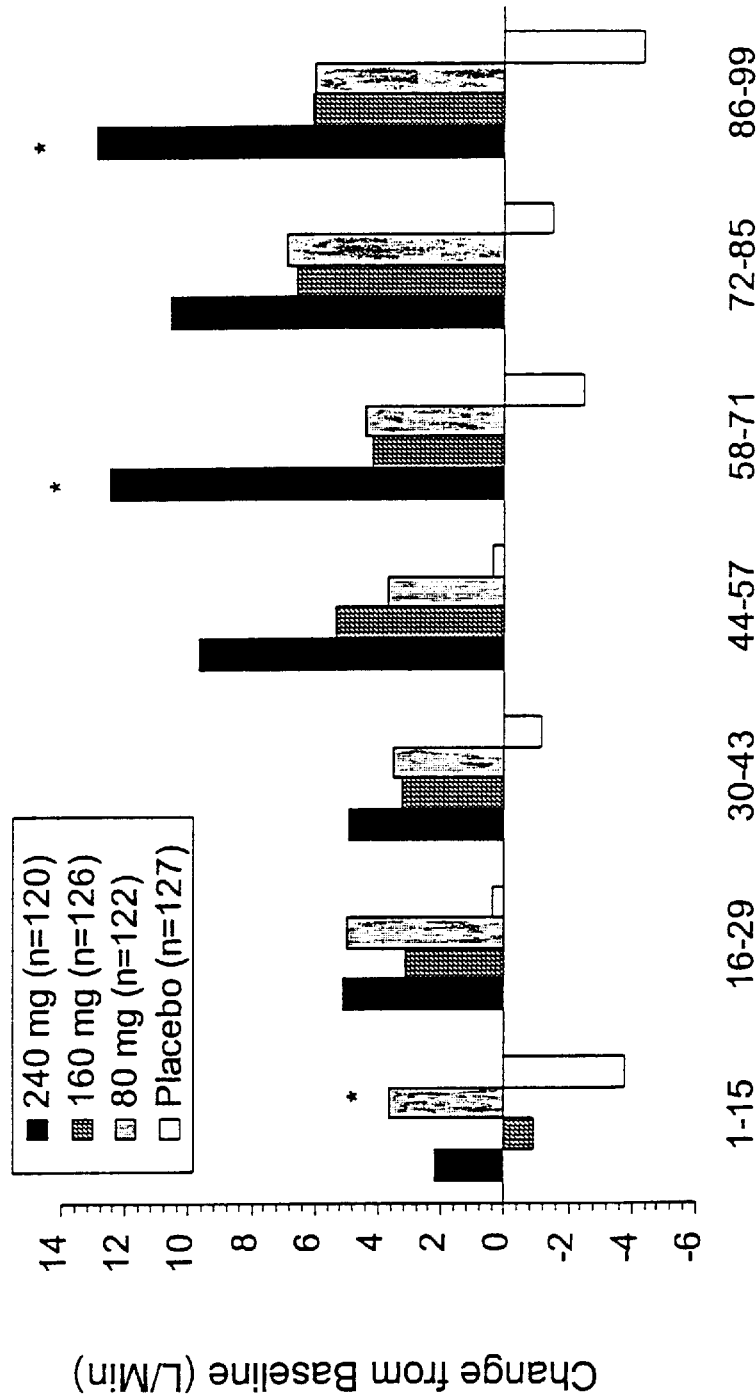
FIGS. 3 and 4 are graphical representations, respectively, of the P. M. and A.M. peak expiratory flow rates for patients taking part in the study.
Figure 4:
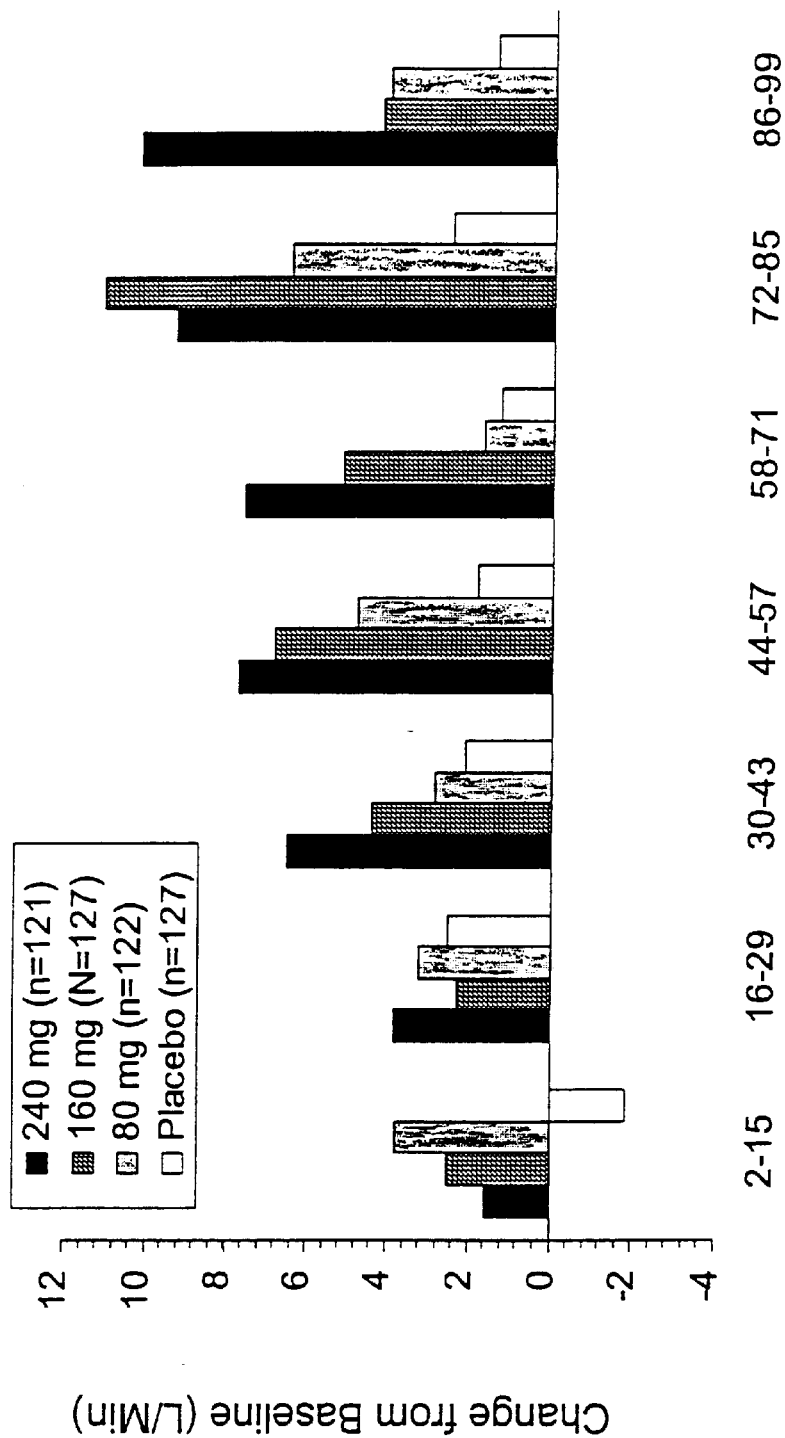

This improvement in $FEV_1$ was also reflected in the P.M. and A.M. PEFR measurements as shown in FIGS. 3 and 4. The 240 mg group showed an 8.8 liter/minute improvement over placebo in the A.M. measurement and a 19.6 liter/minute improvement over placebo in the P.M. measurement (mean values). PEFR reflects day-to-day variation in pulmonary function, and hence an improvement in this function is confirmatory evidence of a lung function benefit.

Figure 5:
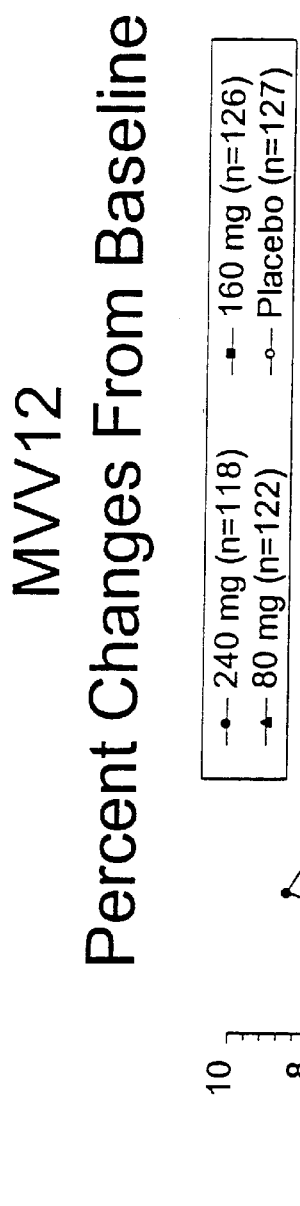
FIG. 5 is a graphical representation of the percent changes from baseline in maximal voluntary ventilation of expiration in twelve seconds ($MVV_{12}$) of patients taking part in the study.

As shown in FIG. 5, $MVV_{12}$ measurements also indicated a favorable trend in the seratrodast groups, with between a 3.2% to 8.0% improvement over placebo.

Figure 6:
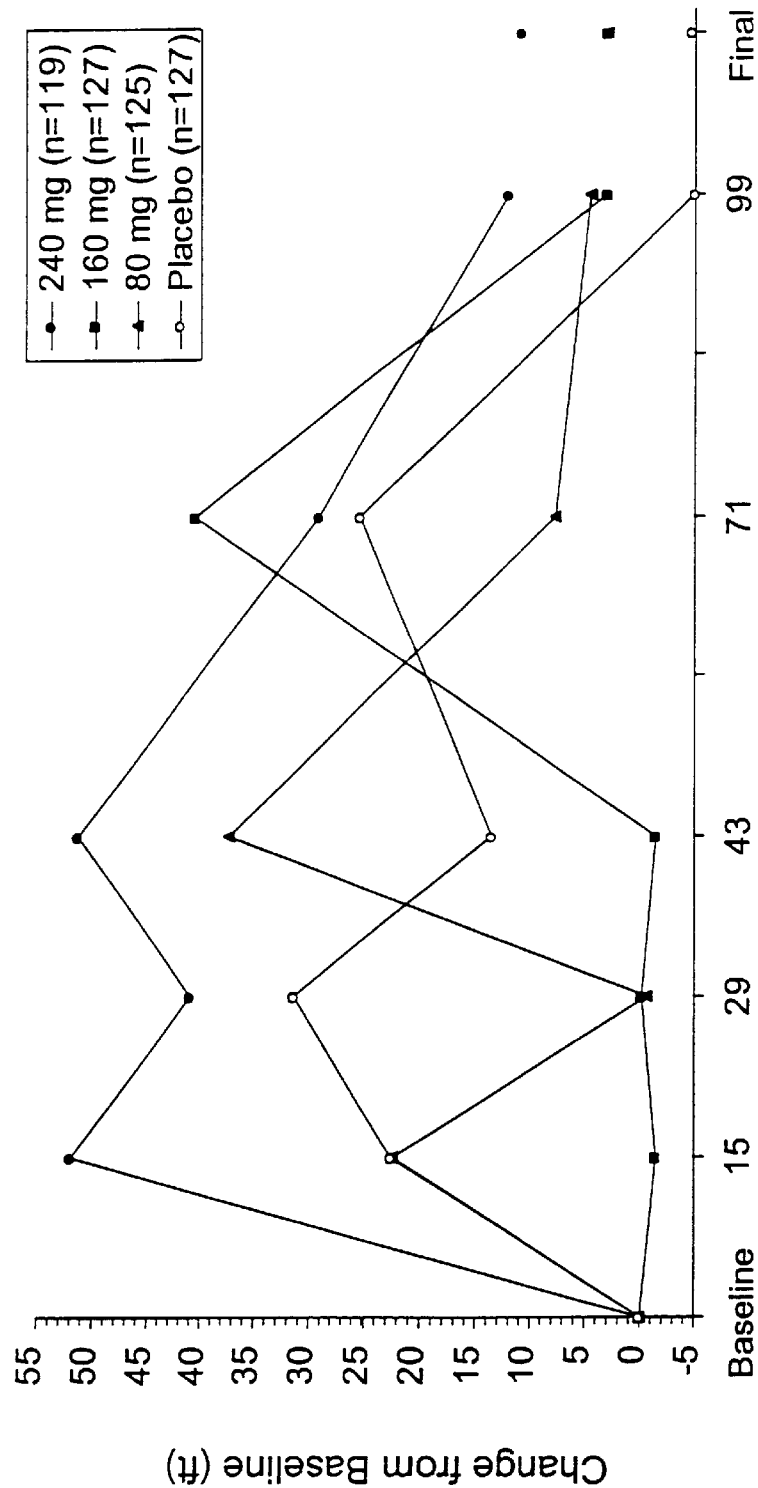
FIG. 6 is a graphical representation of the distance covered by patients in the six-minute walk exercise test.
Figure 7:
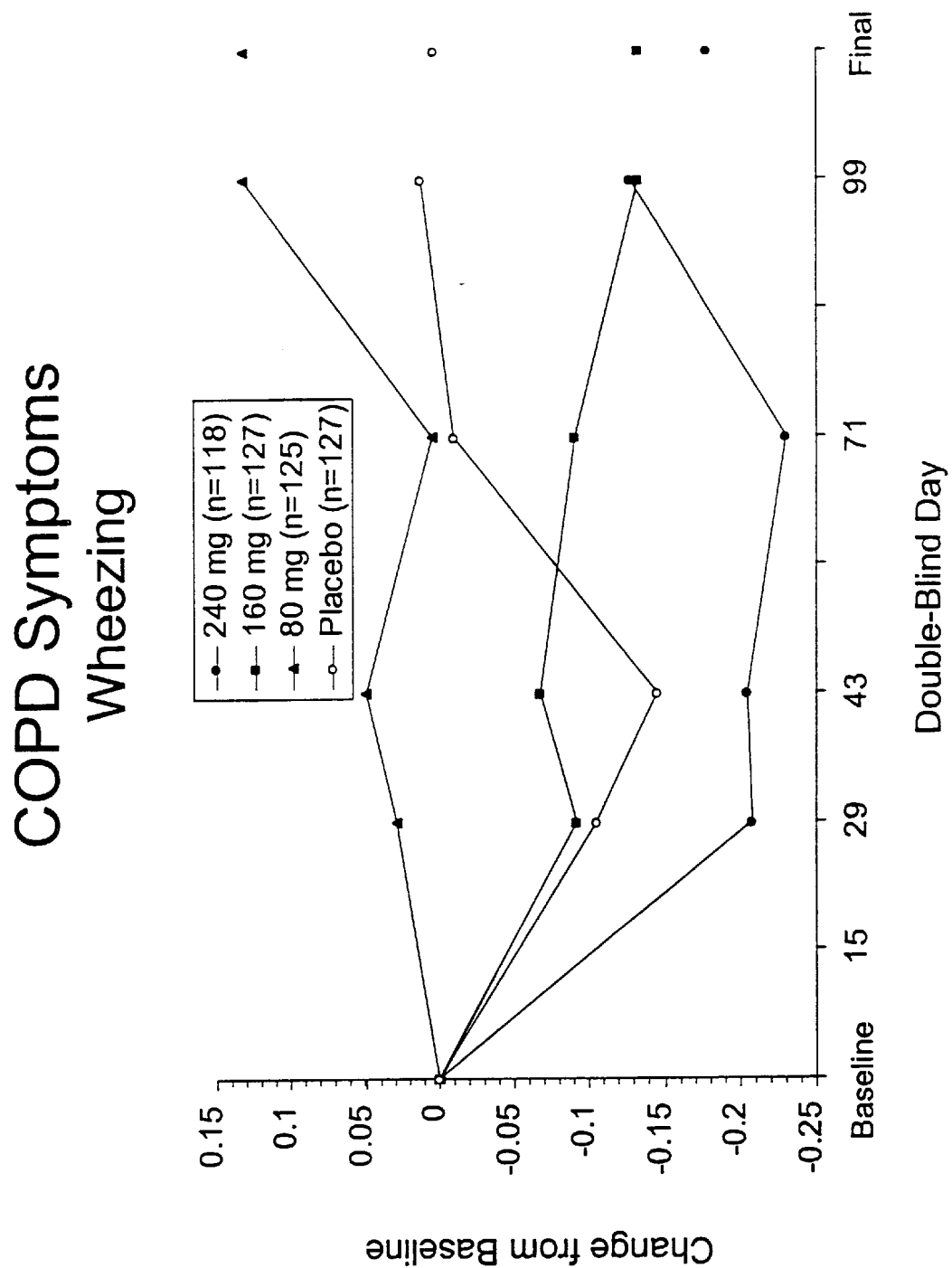
FIG. 7 is a graphical representation of the change from baseline in the COPD wheezing symptom of patients taking part in the study.
Figure 8:
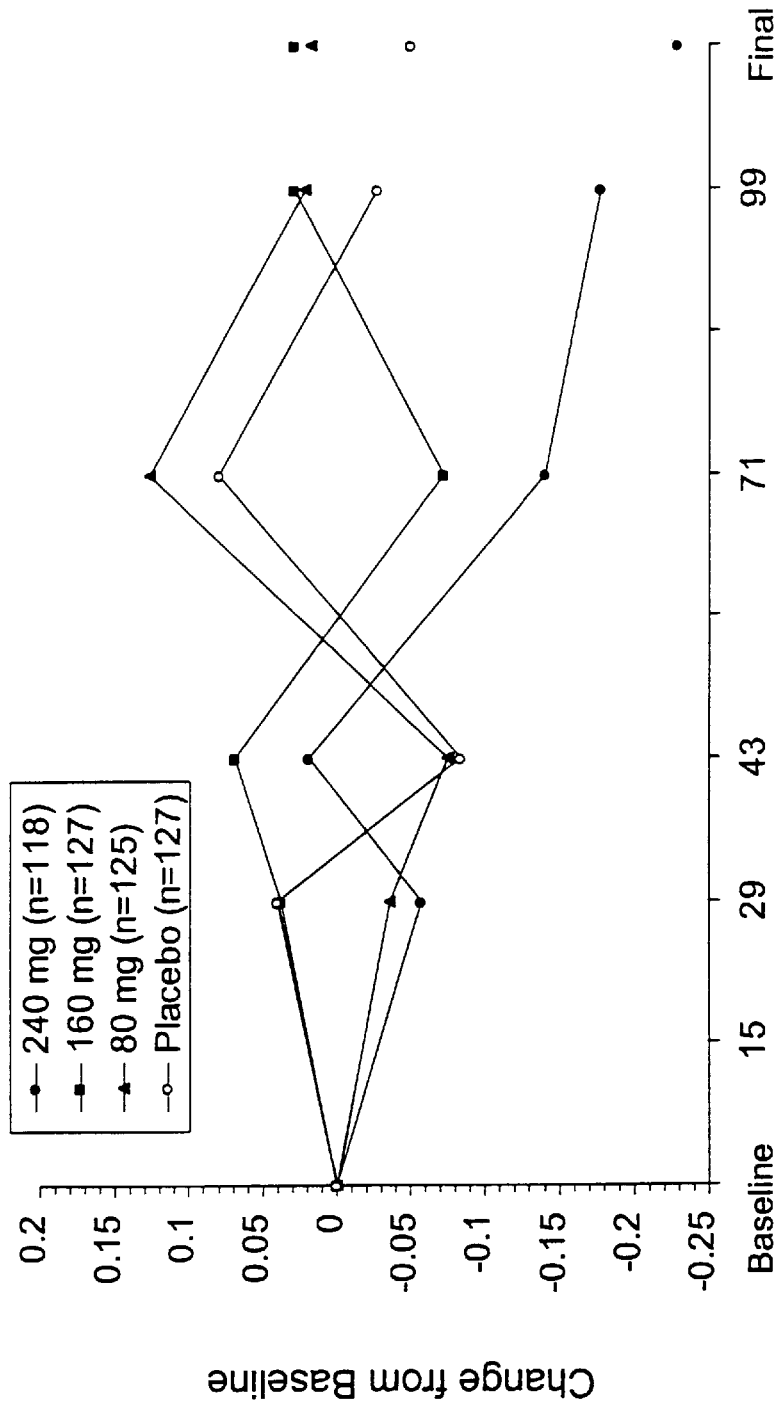
FIG. 8 is a graphical representation of the changes from baseline in COPD chest tightness symptom of patients taking part in the study.
Figure 9:
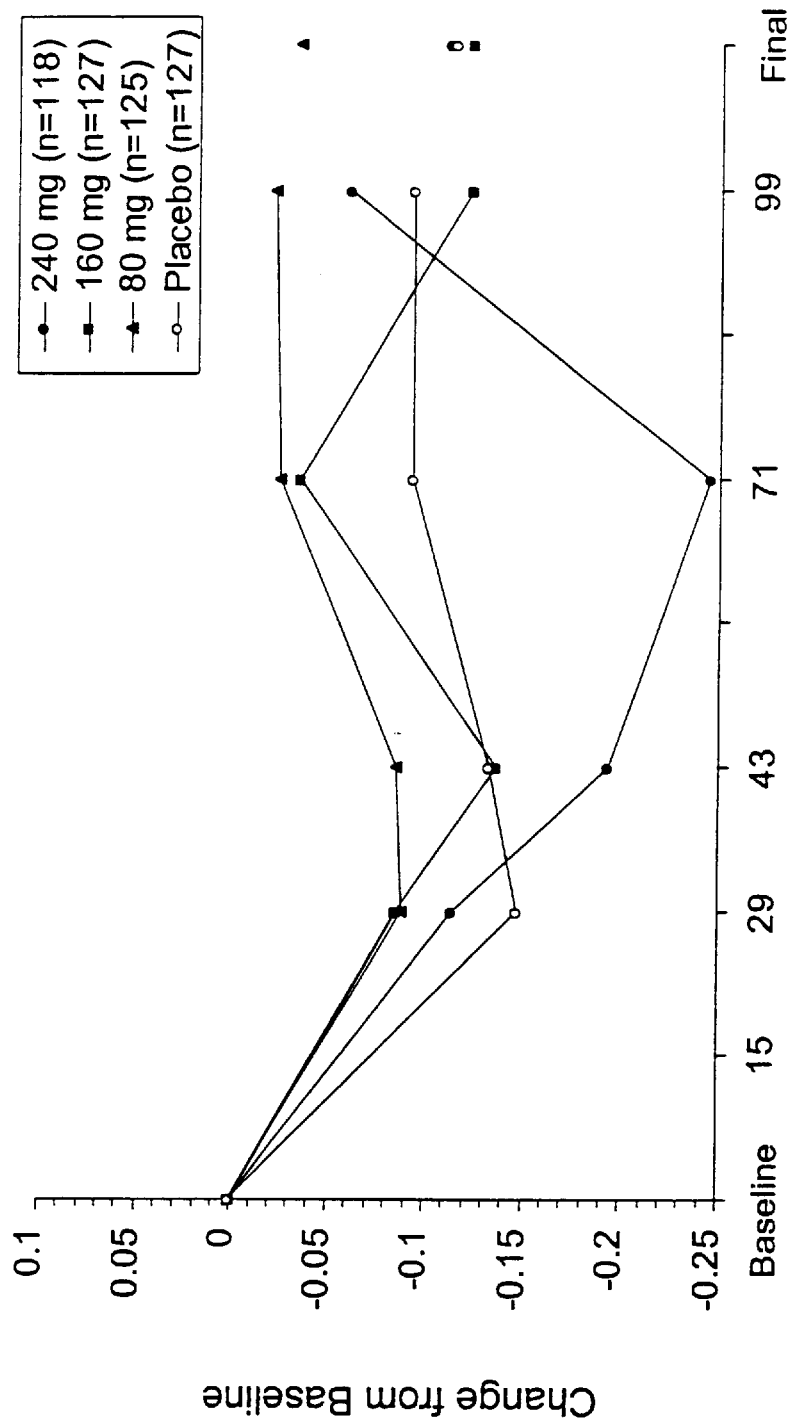
FIG. 9 is a graphical representation of the changes from baseline of COPD cough symptom of patients taking part in the study.
Figure 10:
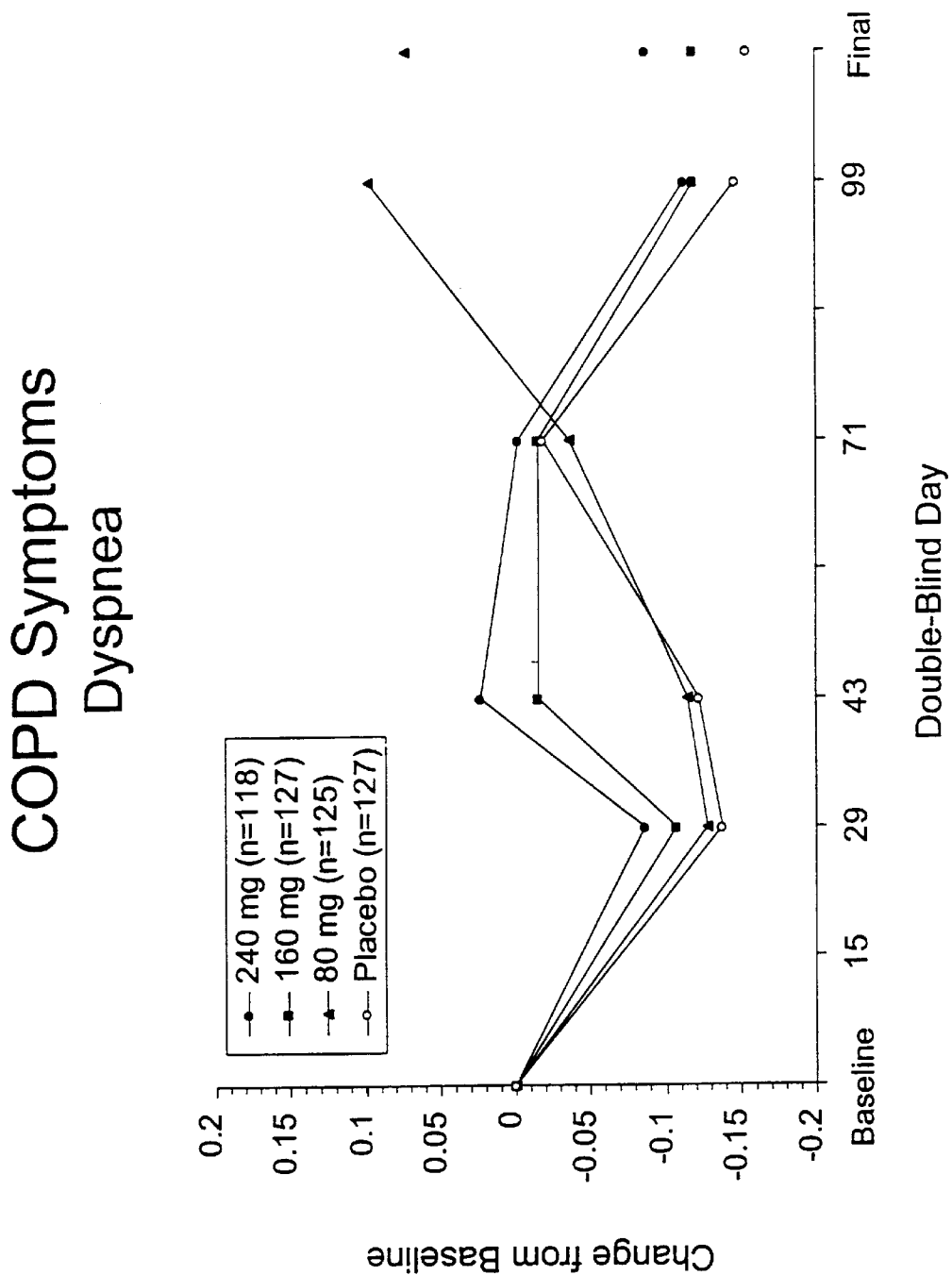
FIG. 10 is a graphical representation of the changes from baseline in COPD dyspnea symptom of patients taking part in the study.
Figure 11:
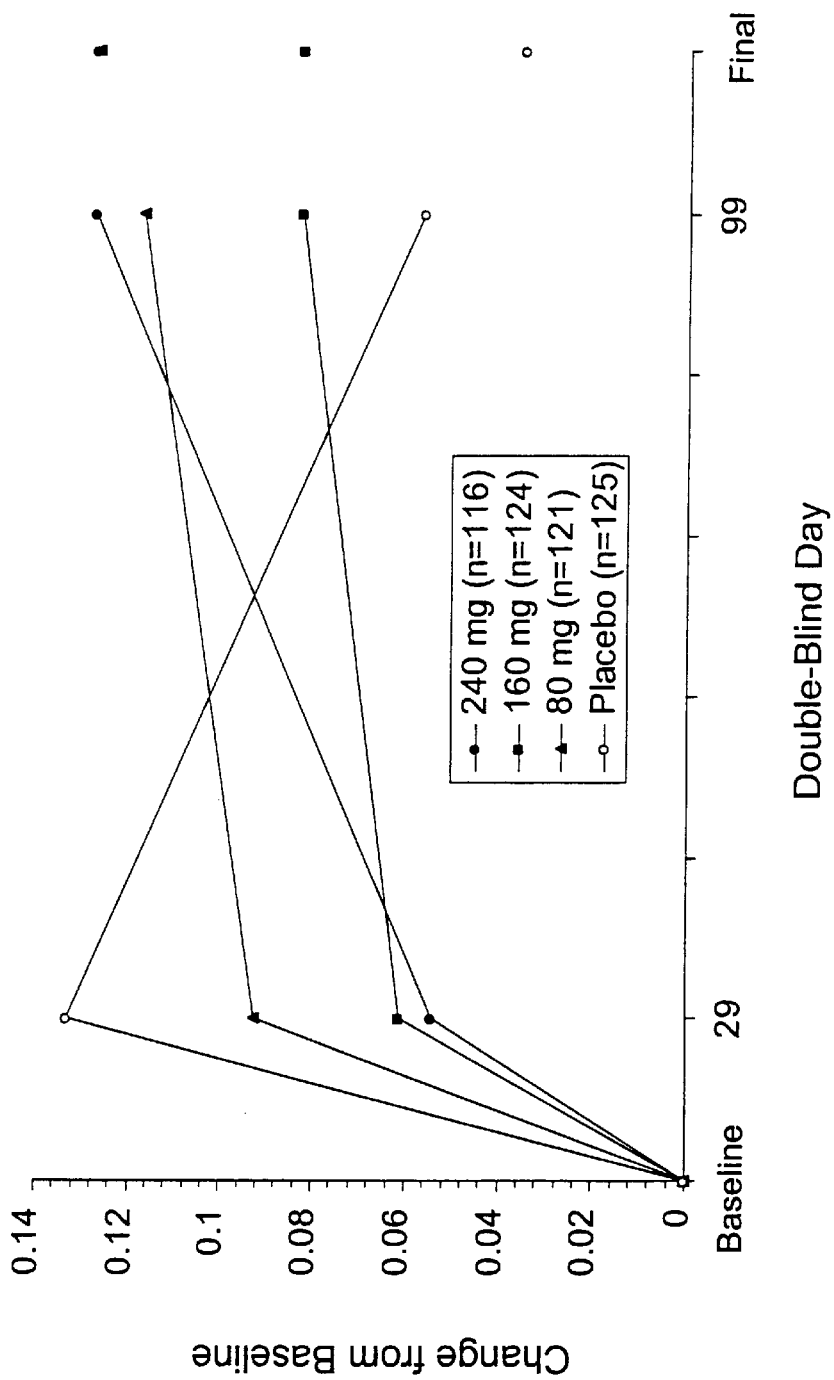
FIG. 11 is a graphical representation of the responses of patients to the Quality of Life Questionnaire with regard to mastery.
Figure 12:
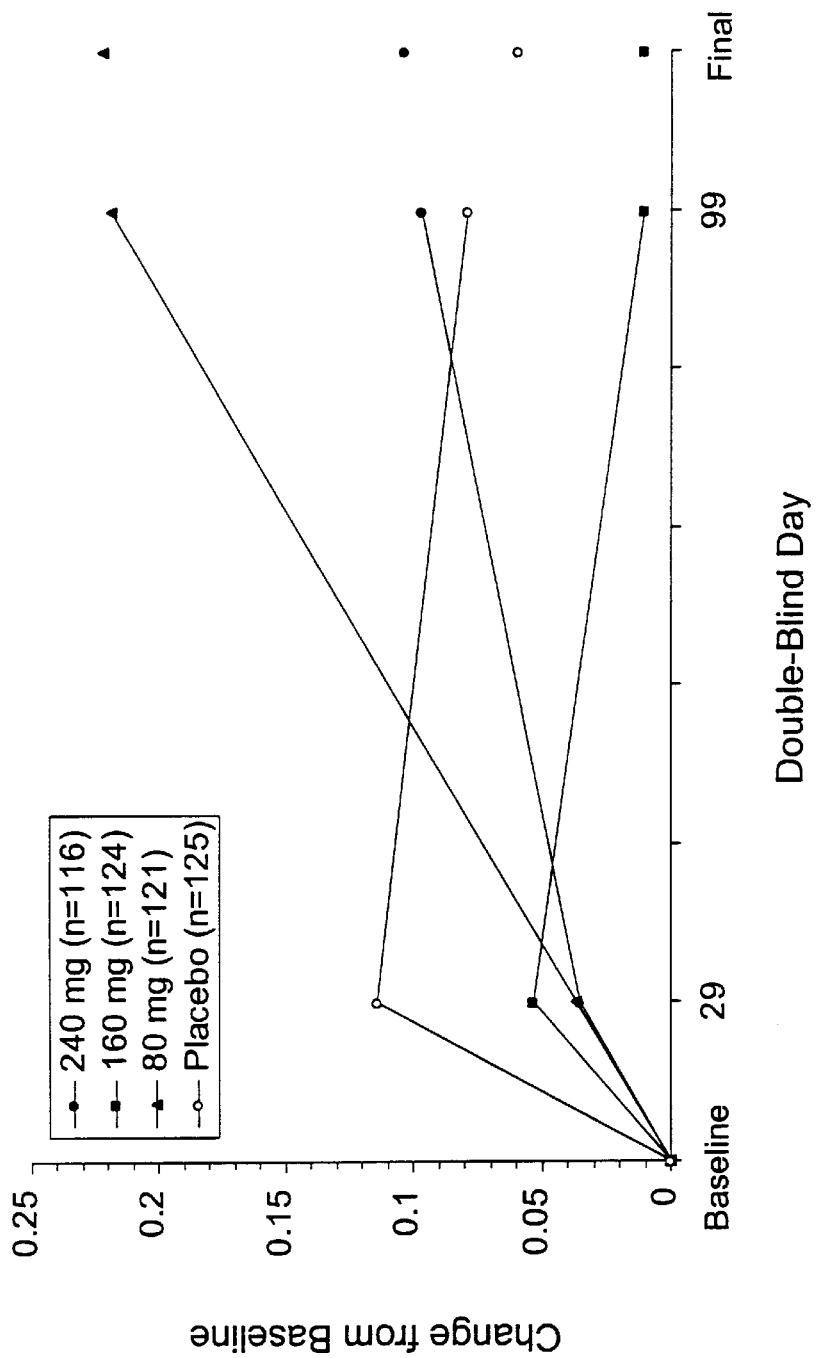
FIG. 12 is a graphical representation of the responses of patients to the Quality of Life Questionnaire with regard to fatigue.
Figure 13:
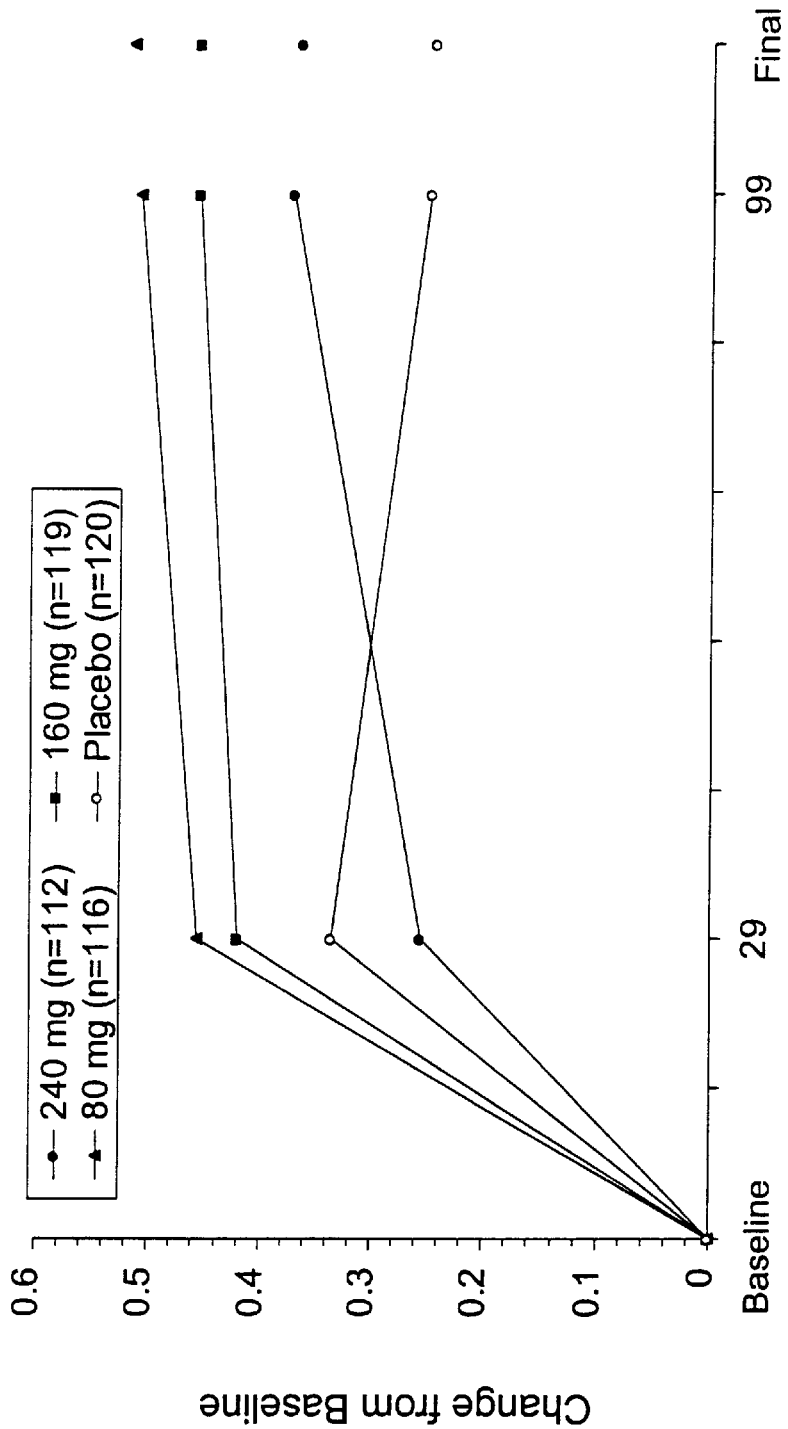
FIG. 13 is a graphical representation of the responses of patients to the Chronic Respiratory Questionnaire with regard to dyspnea.
Figure 14:
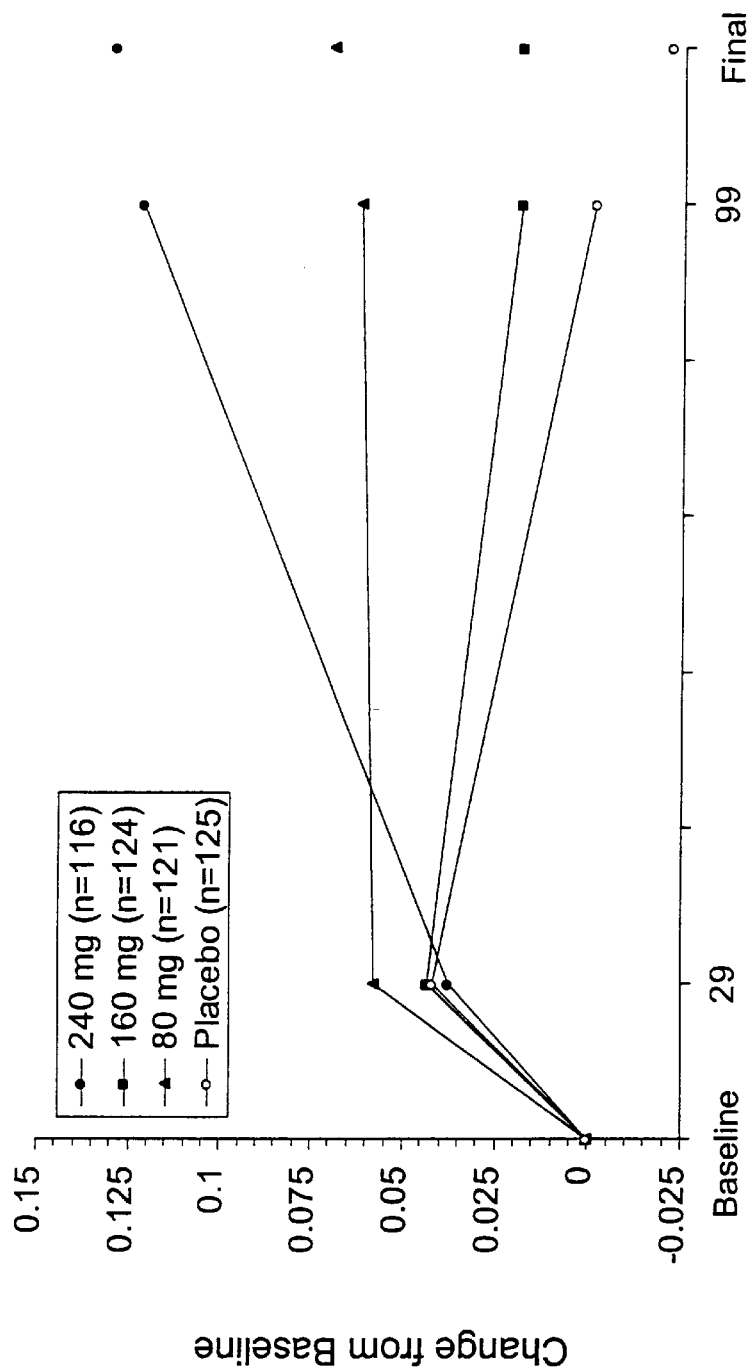
FIG. 14 is a graphical representation of the responses of patients to the Chronic Respiratory Questionnaire with regard to emotional function.

Six-minute walk (distance) was conducted with each patient to reflect the patient's exercise capability. During a six-minute period, each patient was asked to walk back and forth at their own pace between two chairs placed 100 feet apart, covering as much distance as possible in the allotted time. At the end of six minutes, the total distance covered by the patient was measured to the nearest foot, and breathlessness was rated. As shown in FIG. 6, all treated groups showed some benefit in terms of the distance covered when compared with placebo treated groups.

Four primary symptoms of COPD (wheezing, chest tightness, cough, and dyspnea)were measured on a four-point scale. On this scale, 0 represented no symptoms, while 4 represented severe symptoms. Selected seratrodast groups showed a modest benefit compared with placebo for both chest tightness and wheezing, although the drug benefit was not reflected in either the dyspnea or cough measurements (FIGS. 7–10).

The Guyatt's quality of life instrument measured four categories: mastery, fatigue, dyspnea, and emotional functioning on a 1- to 7-point scale. On this scale, 1 represented "worst" and 7 represented "best" in terms of the symptom or quality being measured. Seratrodast-treated patients showed an improvement in all four categories when compared with placebo-treated patients, with the exception of the 160 mg group in the measurement of fatigue (FIGS. 11–14).

Patients also kept a diary during the study and recorded the following: daytime and nighttime symptoms; A.M. and P.M. PEFR (with the aid of a Wright peak flow meter);use of albuterol (beta agonist), recording both the number of occasions of usage each day as well as the number of puffs administered per day.

Figure 15:
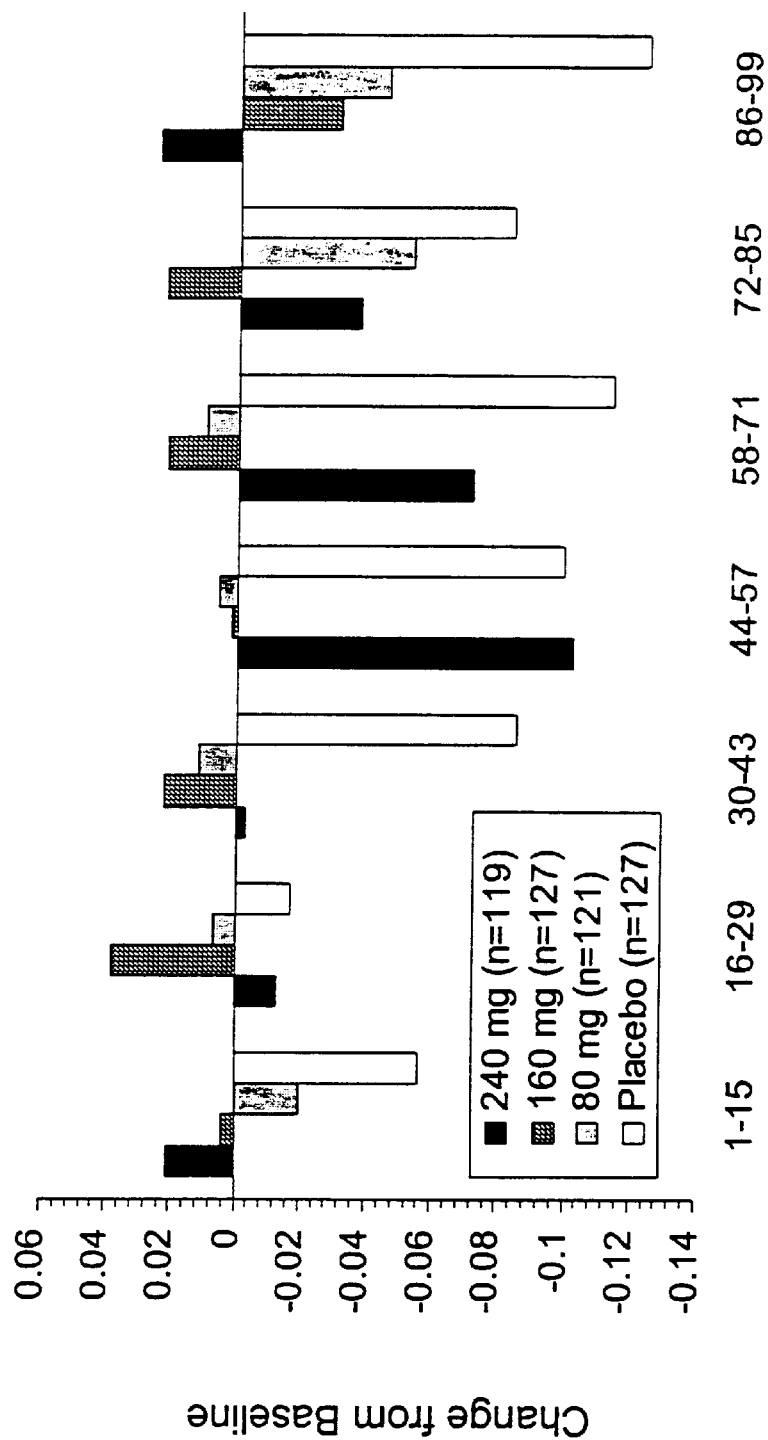
FIG. 15 is a histogram presenting change from baseline in daily symptom assessment of patients taking part in the study.
Figure 16:
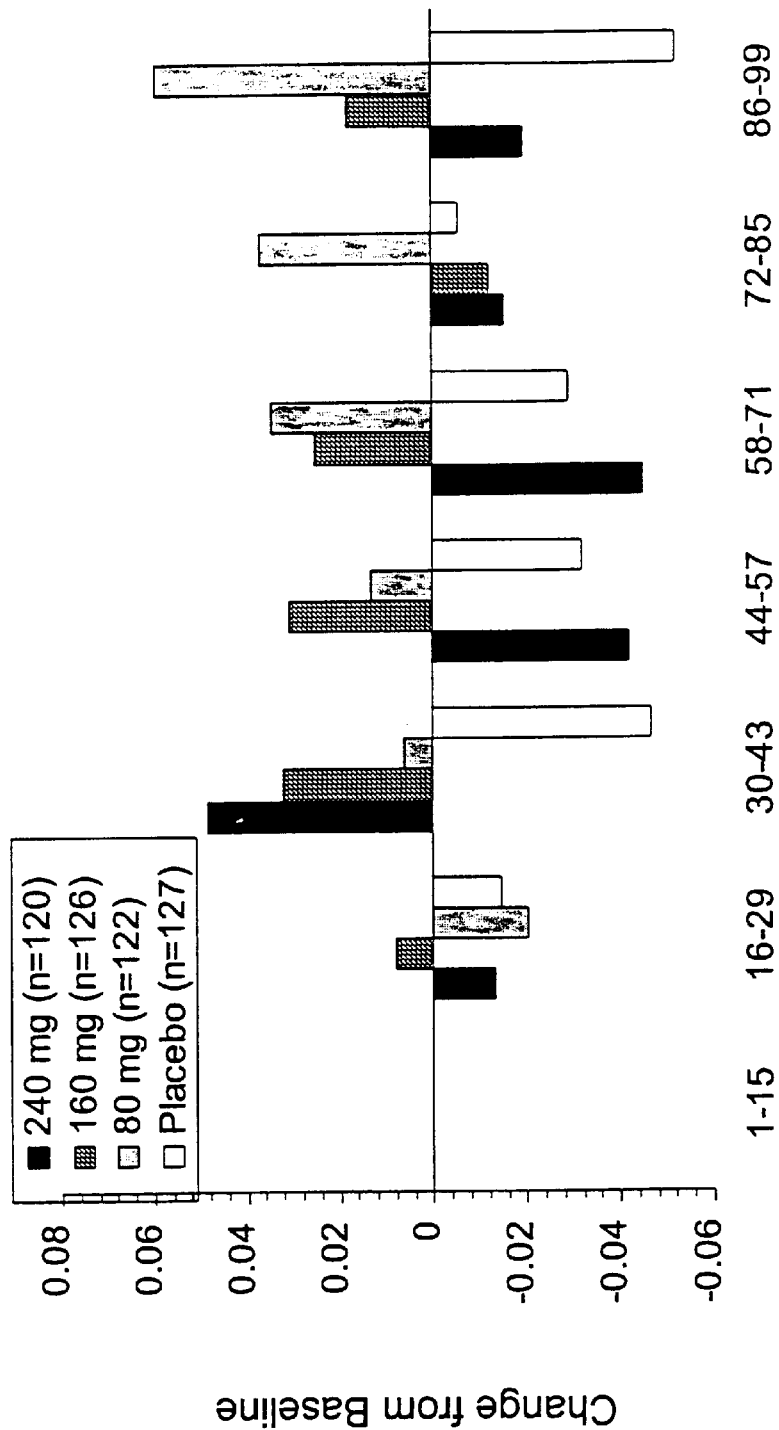
FIG. 16 is a histogram presenting change from baseline in nocturnal symptom assessment of patients taking part in the study.

No differences were observed between the treated and untreated groups in the experience of daytime and nighttime symptoms as recorded in the diaries (FIGS. 15 and 16). However, there was a dramatic improvement in both the A.M. and P.M. PEFR for the patients treated with seratrodast when compared with placebo-treated patients (FIG. 3 (A.M.) and FIG. 4 (P.M.)) This marked drug benefit substantiates the $FEV_1$ effect noted above, and indicates the improvement of lung function with administration of the drug. Beta agonist usage was not significantly affected by treatment with seratrodast, except a trend was observed toward decreased usage in the group treated with 240 mg of seratrodast compared to placebo.

Lastly, cough- and sputum-related symptoms were measured using a Cough and Sputum Index. This questionnaire measured the following categories on a 1–5 or 7 point scale: cough frequency (1–5); cough severity (1–5); cough discomfort/tightness (1"5); need for the use of an aerosol bronchodilator (1–5); and ease in bringing up sputum on arising and throughout the day (1–7).

Figure 17:
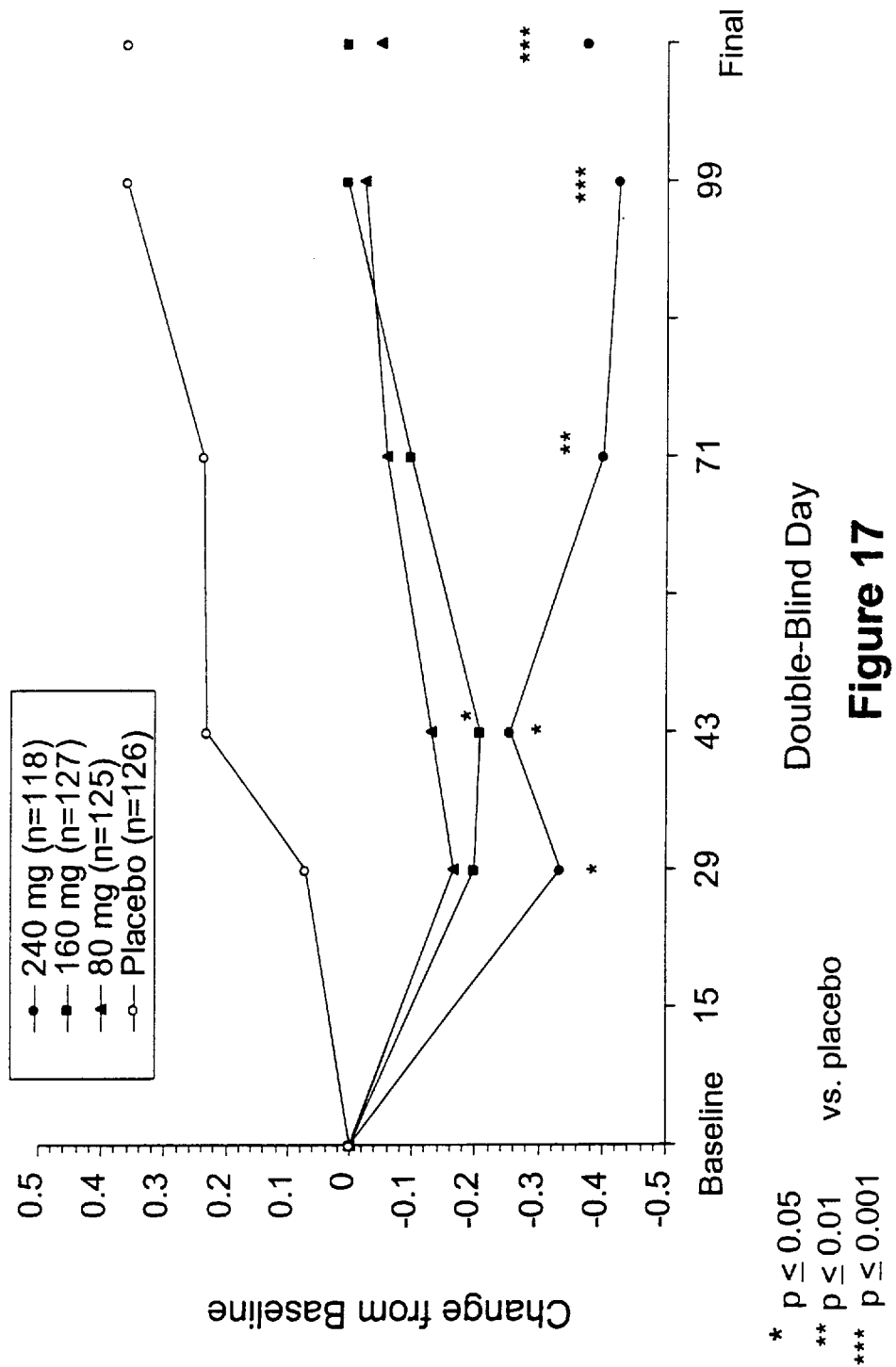
FIG. 17 is a graphical representation of changes from baseline in the ease of bringing up sputum for patients taking part in the study.
Figure 18:
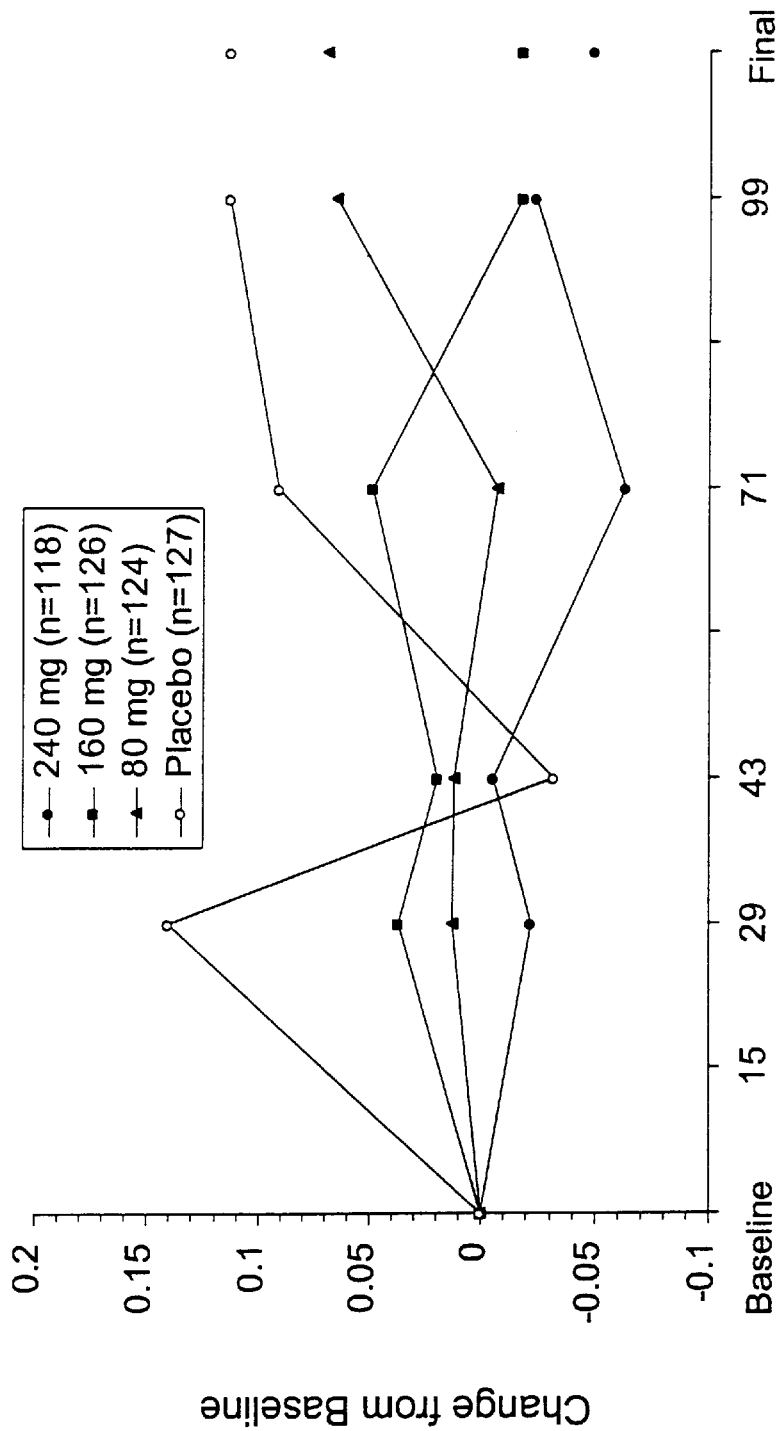
FIG. 18 is a graphical representation of changes from baseline in the need for patients taking part in the study for PRN bronchodilator.
Figure 19:
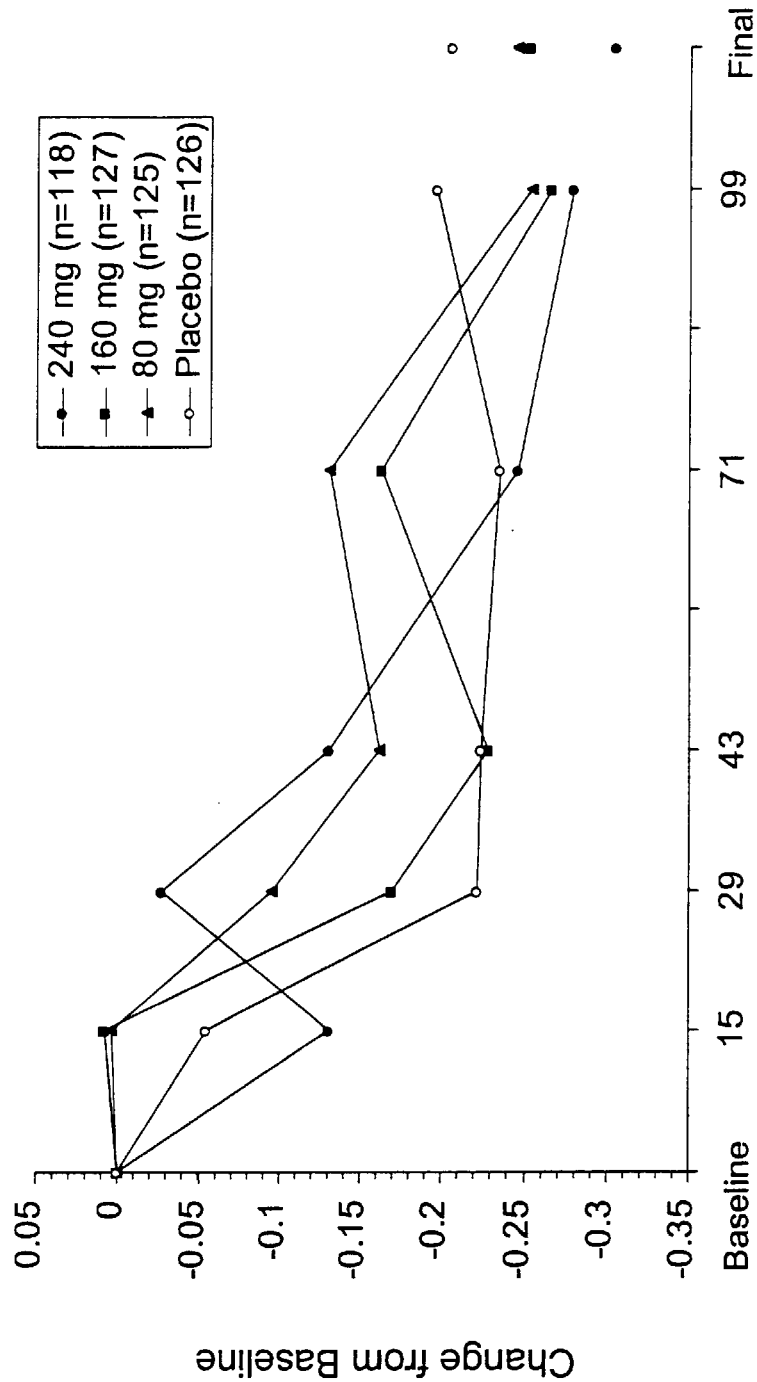
FIG. 19 is a graphical representation of the cough discomfort and tightness/congestion of patients taking part in the study.
Figure 20:
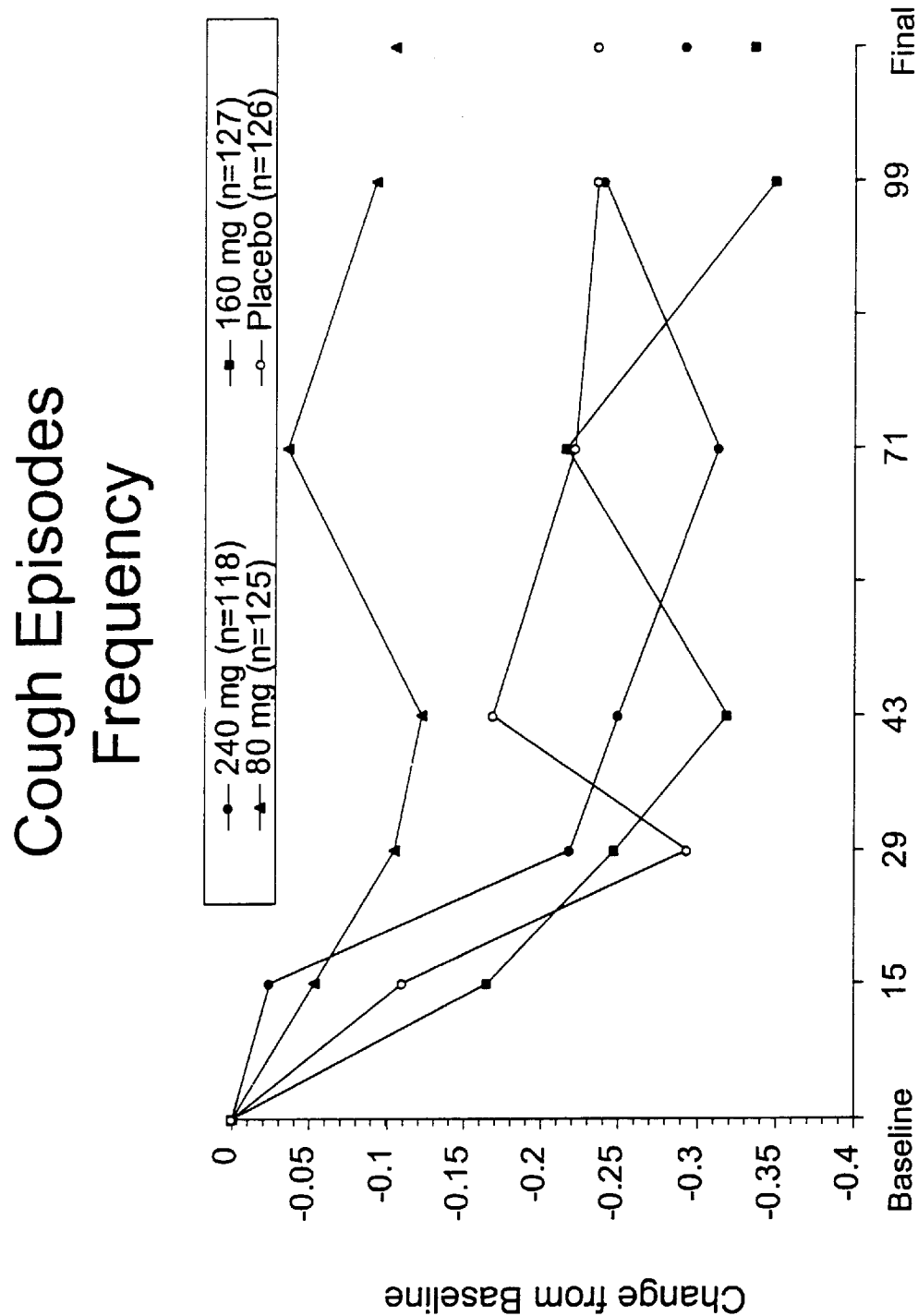
FIG. 20 is a graphical representation of the frequency of cough episodes of patients taking part in the study.
Figure 21:
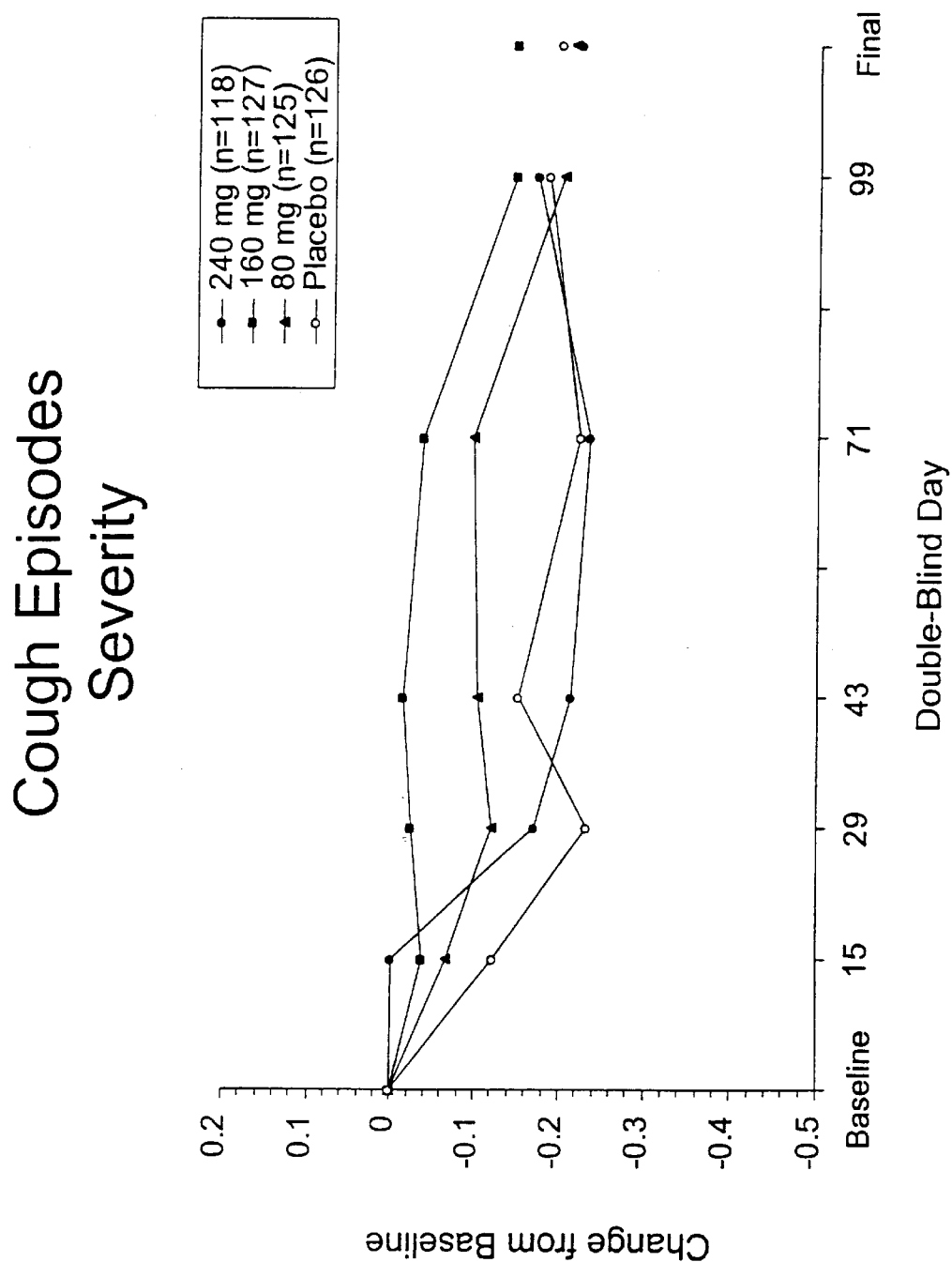
FIG. 21 is a graphical representation of the cough severity of patients taking part in the study.

On these scales, 1 represented mild or absent symptoms, and either 5 or 7 represented worse or more severe symptoms. The results of these questionnaires are shown in FIGS. 17 to 21. The results indicate a substantial benefit in bringing up sputum for all groups receiving seratrodast compared with placebo, with maximum benefit obtained at the 240 mg group (FIG. 17). All groups showed a small decrease in the need for bronchodilator compared with placebo (FIG. 18). In addition, all drug-treated groups showed a small improvement in chest tightness, with the 240 mg group showing the greatest difference from placebo (FIG. 19). For cough frequency and cough severity, two of three seratrodast-treated groups showed a small benefit when compared with placebo-treated groups, however one of the three seratrodast-treated groups in each measure was not as good as placebo (FIGS. 20 and 21).

In total, the data presented in FIGS. 2–21 indicate that administration of (±)-7-(3,5,6-trimethyl-1,4-benzoquinon-2-yl)-7-phenylheptanoic acid (seratrodast) is effective in the treatment of patients suffering from chronic obstructive respiratory disease by ameliorating the progression of the disease, measured as $FEV_1$. Certain symptoms of the disease state were modified by seratrodast treatment as well as improving the patient's quality of life.

While there have been shown and described what are the preferred embodiments of the present invention, they are not to be read as limiting of the scope of the invention as it is defined by the appended claims.

What is claimed is:

1. A method of treating chronic obstructive pulmonary disease in a patient in need of such treatment comprising administering a therapeutically effective amount of a compound of the formula:

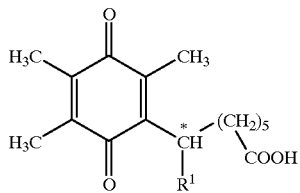

or pharmaceutically acceptable salt or pro-drug thereof, wherein the asterisk denotes a chiral center, and $R^1$ is selected from the group consisting of
  unsubstituted phenyl;
  phenyl substituted with one or more substituents independently selected from the group consisting of
    halo,
    hydroxy,
    alkyl of one to three carbon atoms,
    alkoxy of one to three carbon atoms.

2. A method according to claim 1 wherein said patient in need of treatment suffers from airway obstruction associated with chronic bronchitis.

3. A method according to claim 1 wherein said patient in need of treatment suffers from airway obstruction associated with emphysema.

4. A method according to claim 1 wherein said patient in need of treatment suffers from airway obstruction associated with both chronic bronchitis and emphysema.

5. The method according to claim 2 wherein said patient in need of treatment is asthmatic.

6. The method according to claim 3 wherein said patient in need of treatment is asthmatic.

7. The method according to claim 4 wherein said patient in need of treatment is asthmatic.

8. A method of treating chronic obstructive pulmonary disease comprising administering to a patient in need of such treatment a therapeutically effective amount of a compound having the name (±)7-(3.4.5-trimethyl-1,4-benzoquinon-2-yl)-7-phenylheptanoic acid or a pharmaceutically acceptable salt or pro-drug thereof.

9. A method according to claim 8 wherein said patient in need of treatment suffers from airway obstruction associated with chronic bronchitis.

10. A method according to claim 8 wherein said patient in need of treatment suffers from airway obstruction associated with emphysema.

11. A method according to claim 8 wherein said patient in need of treatment suffers from airway obstruction associated with both chronic bronchitis and emphysema.

12. The method according to claim 9 wherein said patient in need of treatment is asthmatic.

13. The method according to claim 10 wherein said patient in need of treatment is asthmatic.

14. The method according to claim 11 wherein said patient in need of treatment is asthmatic.

15. A method of treating chronic obstructive pulmonary disease comprising administering to a patient in need of such treatment a therapaeutically effective amount of a compound having the name R(+)-7-(3,5,6-trimethyl-1,4-benzoquinon-2-yl)-7-phenyl-heptanoic acid or a pharmaceutically acceptable salt or pro-drug thereof.

16. A method according to claim 15 wherein said patient in need of treatment suffers from airway obstruction associated with chronic bronchitis.

17. A method according to claim 15 wherein said patient in need of treatment suffers from airway obstruction associated with emphysema.

18. A method according to claim 15 wherein said patient in need of treatment suffers from airway obstruction associated with both chronic bronchitis and emphysema.

19. The method according to claim 16 wherein said patient in need of treatment is asthmatic.

20. The method according to claim 17 wherein said patient in need of treatment is asthmatic.

21. The method according to claim 18 wherein said patient in need of treatment is asthmatic.

22. A method of treating chronic obstructive pulmonary disease comprising orally administering to a patient in need of such treatment a daily dose ranging between about 50 and 1000 mg of a compound having the name (±)-7-(3,5,6-trimethyl-1,4-benzoquinon-2-yl)-7-phenyl-heptanoic acid or a pharmaceutically acceptable salt or pro-drug thereof.

23. The method according to claim 22 wherein the method of administration is orally.

24. The method of claim 22 wherein said compound is the (R+)-enantiomer or a pharmaceutically acceptable salt or pro-drug thereof.

* * * * *